US005700686A

United States Patent [19]
Foody et al.

[11] Patent Number: 5,700,686
[45] Date of Patent: Dec. 23, 1997

[54] PROTEASE-TREATED AND PURIFIED CELLULASE COMPOSITIONS AND METHODS FOR REDUCING BACKSTAINING DURING ENZYMATIC STONEWASHING

[75] Inventors: Brian Foody; Colin Nicholson; Jeffrey Tolan; Theresa White, all of Ottawa, Canada

[73] Assignee: Iogen Corporation, Ottawa, Canada

[21] Appl. No.: 466,424

[22] Filed: Jun. 6, 1995

[51] Int. Cl.$^6$ .......................... D06M 16/00; C12N 9/42; C12N 1/14; C12N 1/00

[52] U.S. Cl. ...................... 435/263; 435/209; 435/254.6; 435/945

[58] Field of Search ............................... 435/209, 263, 435/254.6, 945

[56] References Cited

U.S. PATENT DOCUMENTS

| | | |
|---|---|---|
| 4,832,864 | 5/1989 | Olson .................................. 8/401 |
| 4,912,056 | 3/1990 | Olson .................................. 435/263 |
| 5,246,853 | 9/1993 | Clarkson et al. ..................... 435/263 |

FOREIGN PATENT DOCUMENTS

| | | |
|---|---|---|
| 0215594 | 3/1987 | European Pat. Off. . |
| 0244234 | 11/1987 | European Pat. Off. . |
| WO9305226 | 3/1993 | WIPO . |
| WO9325655 | 12/1993 | WIPO . |
| WO9426925 | 11/1994 | WIPO . |
| WO9429426 | 12/1994 | WIPO . |
| WO9516782 | 6/1995 | WIPO . |

OTHER PUBLICATIONS

Vesa V. Joutsjoki, "Construction by one–step gene replacement of Trichoderma reesei strains that produce the glucoamylase P of Hormoconis reesei", Current Genetics, pp. 422–429 (1994).

Ritva Saarelainen, et al., "Cloning, sequencing and enhanced expression of the Trichoderma reesei endoxylanase II (pI 9) gene xln2", Mol Gen Genet, vol. 241, pp. 497–503 (1993).

Taina Karhunen, et al., "High frequency one–step gene replacement in Trichoderma reesei. I. Endoglucanase I overproduction", Mol Gen Genet, Vo. 241, pp. 515–522 (1993).

P.H. Nielsen, et al, "Enzyme Applications (Industrial and Therapeutic)", Encyclopedia of Chemical Technology, vol. 9, pp. 567–620 (1993).

"Ion Exchange Chromatography: Principles and Methods," Pharmacia, Laboratory Separation Division, pp. 1–71 (1988).

T.K. Ghose, "Measurement of Cellulase Activities", International Union of Pure and Applied Chemistry, vol. 59, No. 2, pp. 257–268 (1987).

D. Kochavi, et al., "Optimizing Processing Conditions in Enzymatic Stonewashing", American Dystuff Reporter, pp. 24–28 (Sep. 1990).

H. Chen, et al., "Three Forms of Cellobiohydrolase I From Trichoderma Reesei" Biochemistry and Molecular Biology International, vol. 30, No. 5, pp. 901–910 (Aug. 1993).

J. Woodward, et al., "Papain Digestion of Crude Trichoderma Reesei Cellulase: Purification and Properties of Cellobiohydrolase I and II Core Proteins", Biotechnol. Appl. Biochem., vol. 19, pp. 141–153 (1994).

H.V. Tilbeurgh, et al., "Limited Proteolysis of the Cellobiohydrolase I from Trichoderma Reesei", Separation of Functional Domains, Federation of European Biochem. Societies, vol. 204, No. 2, pp. 223–227 (Aug. 1986).

P. Tomme, et al., "Studies of the Cellulolytic System of Trichoderma Reesei QM 9414", Analysis of Domain Function in Two Cellobiohydrolases by Limited Proteolysis, Eur. J. Biochem. vol. 170, pp. 575–581 (1988).

D.A. Offord, et al., "Preparative Purification of Trichoderma Reesei Native and Core Cellobiohydrolase I by Electrophoresis and Chromatofocusing", Scientific Note, Applied Biochemistry and Biotechnology, vol. 28, No. 29, pp. 377–386 (1991).

H.C. Chen, et al., "Effect of Cellulase Size Reduction on Activity and Accessibility", Biotechnology Letters, vol. 10, No. 12, pp. 913–918 (1988).

J. Mohammad, et al., "Real–Time Kinetic Analysis of Limited Proteolysis By Ion–Exchange Chromatography Using Compressed, Non–Porous Agarose Beads", Journal of Biochemical and Biophysical Methods, pp. 41–49 (1993).

J. Woodward, et al., "Does Cellobiohydrolase II Core Protein From Trichoderma Reesei Disperse Cellulose Microfibrils?", Enzyme Microb. Technol., vol. 14, pp. 625–630 (Aug. 1992).

IndiAge Euro–L Denim–Washing Enzyme, Delivering Innovation Through Biotechnology, Genencor International (1993).

D.E. McEwan, et al., "Euro Technology", Genencor International, Inc., Proceedings of the AATCC Garment Wet Processing Symposium, pp. 1–8 (1995).

C.M.G.A. Fontes, et al, "The Resistance of Cellulase and Xylanases to Proteolytic Inactivation", Appl. Microbiol. Biotechnol., vol. 43, pp. 52–57 (1995).

S. Akiba, et al., "Effects of Size of Carbohydrate Chain on Protease Digestion of Aspergillus Niger Endo–β–1,4–Glucanase", Biosci. Biotech. Biochem., vol. 59, No. 6, pp. 1048–1051 (1995).

(List continued on next page.)

Primary Examiner—Leon B. Lankford, Jr.
Assistant Examiner—Christopher R. Tate
Attorney, Agent, or Firm—Fitzpatrick, Cella, Harper & Scinto

[57] ABSTRACT

During the enzymatic "stone washing" of a denim fabric and/or garments, an undesirable redeposition of blue dye often occurs on the surfaces of the denim. The invention relates to a means of overcoming this problem using an enzyme composition comprised of Trichoderma endoglucanase and Trichoderma cellobiohydrolase that has been partially digested by a protease enzyme to separate its core and binding domains. The use of this composition reduces the redeposition of the blue dye and hence improves the stone washing process relative to using a redepositing or backstaining cellulase.

23 Claims, No Drawings

OTHER PUBLICATIONS

N. Din, et al., "$C_1$–$C_x$ Revisited: Intramolecular Synergism in a Cellulase", Proc. Natl. Acad. Sci. USA, vol. 91, pp. 11383–11387 (Nov. 1994).

J.B. Coutinho, et al., "The Nature of the Cellulose–Binding Domain Affects the Activities of a Bacterial Endoglucanase on Different Forms of Cellulose", FEMS Microbiology Letters, vol. 113, pp. 211–218 (1993).

N. Din, et al., "Non–Hydrolytic Disruption of Cellulose Fibres by the Binding Domain of a Bacterial Cellulase", Bio/Technology, vol. 9, pp. 1096–1099 (Nov. 1991).

N.R. Gilkes, et al., "Structural and Functional Analysis of a Bacterial Cellulase by Proteolysis", The Journal of Biological Chemistry, vol. 264, No. 30, pp. 17802–17808 (Oct. 25, 1989).

N.R. Gilkes, et al., "Precise Excision of the Cellulose Binding Domains from Two *Cellulomonas fimi* Cellulases by a Homologous Protease and the Effect on Catalysis", The Journal of Biological Chemistry, vol. 263, No. 21, pp. 10401–10407 (Jul. 25, 1988).

M.L. Langsford, et al., "Glycosylation of Bacterial Cellulases Prevents Proteolytic Cleavage Between Functional Domains", FEBS, vol. 225, No. 1, 2, pp. 163–167 (Dec. 1987).

IndiAge Euro–L Denim–Washing Enzyme, Delivering Innovation Through Biotechnology, Genencor International (1995).

PROTEASE-TREATED AND PURIFIED CELLULASE COMPOSITIONS AND METHODS FOR REDUCING BACKSTAINING DURING ENZYMATIC STONEWASHING

FIELD OF THE INVENTION

This invention relates to compositions and methods for reducing or preventing the backstaining of blue indigo dye onto denim during the stonewashing of denim fabric and garments utilizing cellulase enzymes.

BACKGROUND OF THE INVENTION

Denim is a woven cotton cloth wherein the warp thread has been dyed, usually blue, with the dye, indigo. One desirable characteristic of indigo-dyed denim cloth is the look created by the alternating blue and white threads of the warp and weft yarns, which upon normal wear and tear gives denim a white on blue appearance. A popular look for denim is the stonewashed look. This stonewashed look consists a generally lighter blue color than unwashed denim with localized areas, particularly around the seams, of even lighter color. Stonewashed material often has a softer texture and maintains the desirable white on blue contrast. Traditionally, stonewashing has been performed by laundering the denim material in the presence of pumice stone, which results in fabric having a faded or worn appearance and desired white on blue contrast described above. Enzymes, particularly cellulases, are currently used in processing denim. In particular, cellulases are used to give denim a stonewashed appearance without the need for as high a loading of the pumice stones that are used in traditional stonewashing. This processing method is referred to herein as enzymatic "stonewashing", even if no stones are present in the washer. Use of enzymes to stonewash has become increasingly popular because use of stones has several disadvantages. For example, stones used in the process cause wear and tear on the machinery, environmental waste problems due to the grit produced and result in high labor costs associated with the manual removal of the stones from the machines and the pockets of garments. Consequently, reduction or elimination of stones in wash may be desirable.

Contrary to the use of pumice stones, enzymes (particularly cellulases) are safe for the machine, result in little or no waste problem and drastically reduce labor costs. Therefore, it may be beneficial to use enzymes for stonewashing. However, even though the use of enzymes such as cellulase may be beneficial as compared to stones, there are some problems associated with the use of enzymes for this purpose. For example, one problem with some cellulases, such as cellulases from the wood-rotting fungus Trichoderma, is what could be described as a "redeposition" or "backstaining" (both terms used interchangeably herein) of some of the dye back onto the fabric during the enzymatic stonewashing process. Such redeposition or backstaining leads to a blue coloration on the white denim threads, resulting in less contrast between the blue and white threads and abrasion points (i.e., a blue on blue look rather than the preferred white on blue). See American Dyestuff Reporter, September 1990, pp. 24–28.

Redeposition or backstaining is objectionable to some users. For example, even though Trichoderma cellulases exhibit a much higher specific activity on denim material than Humicola cellulases, cellulases from Humicola are often preferred because of their lower level of backstaining. This is so, even though the much higher potency of Trichoderma cellulase permits the use of smaller quantities of enzyme to achieve a higher degree of abrasion in significantly shorter processing times.

The problem of redeposition of dye during stonewashing has been a concern of denim processors. Previous attempts to address the problem with Trichoderma cellulase compositions include addition of extra anti-redeposition chemicals, such as surfactants or other agents, into the cellulase wash to help disperse the loosened indigo dye and reduce redeposition. In addition, denim processors have tried using cellulases with less specific activity on denim, along with extra rinsings. This results in additional chemical costs and longer processing times. Another method attempting to address the redeposition problem includes adding a mild bleaching agent or stain removing agent in the process. This method affects the final shade of the garment and increases processing time.

While these methods aid to some limited degree in the reduction of redeposition, the methods are not entirely satisfactory and some objectionable backstaining remains. Use of enzymes and stones together may be advantageous in decreasing the degree of redeposition) however, it leaves the processor with some of the problems associated with the use of stones alone.

Another method, as described by Clarkson et al in PCT Publication No. WO 94/29426 (hereafter "Clarkson et al"), has been to include an added protease enzyme in the stone washing treatment. It was found that the treatment of denim with a composition comprising a redepositing cellulase and an added protease improves the contrast between white and blue threads and reduces dye redeposition. Acting in the washing machine, the proteases are somehow thought to prevent the cellulase proteins from binding the colored particles back onto the surface of the denim, and yet, when used in moderation, they do not have a severe adverse effect on the resultant abraded look caused by the action of the cellulase. This method, while providing some advantages, is costly and requires careful control because proteases, by their very nature, tend to destroy cellulase enzymes. The practitioner must strike a balance between the desirable proteolytic effect on reducing backstaining and the undesirable proteolytic effect on reducing the activity of the cellulase.

In the process of Clarkson et al, the protease is used essentially as a stain remover or staining inhibitor and must be included in the washing process. Clarkson et al teach three options; (1) add the protease directly to the washer with the cellulase enzyme, (2) add the protease to the rinse cycle after a cellulase treatment, or (3) blend the protease with the cellulase prior to washing. Relative to the basic process of adding the protease and cellulase together, adding the protease to the rinse cycle avoids significant proteolytic attack on the cellulase, but it has the disadvantage of adding an extra processing step. Pre-blending the cellulase and protease, on the other hand, makes for a simple easy-to-use formulation, but results in a difficult balance between the desirable proteolytic effect on stain removal and the undesirable proteolytic effect on destroying cellulase activity. For example, a highly active protease may completely destroy the cellulase enzyme during the normal time it takes for storage and shipping. This shelf stability problem can be managed but requires; (1) selection of a protease that has good anti-staining power, but can digest cellulase to, at most, a limited extent, (subtilisins, which are not highly active against cellulase but are well known as potent stain removers are a preferred choice), and (2) a pre-incubation of the selected protease and cellulase at an elevated temperature to ensure that what proteolytic attack there is on the cellulase is taken to completion and that a commercial formulation will be stable during storage and shipping.

The action of stronger proteases, particularly the protease papain on Trichoderma cellulases, has been investigated extensively. It has been found that limited amounts of papain digestion can split the core domains of Trichoderma cellobiohydrolases apart from their natural binding domains. This has the effect of essentially eliminating any measurable activity these enzymes have against crystalline cellulose such as Avicel or cotton while still preserving their activity against soluble substrates such as β-glucan. As a result, prior workers concluded that the natural binding domain plays a critical role in enabling the cellobiohydrolase enzyme's attack on crystalline cellulose. The extent of treatment needed for papain to completely eliminate CBH activity on crystalline cellulose was roughly 0.1 to 0.5 grams of papain protein per gram of cellulase protein, all multiplied by the treatment time in minutes (g min/g), that is, weight ratio of protease protein to cellulase protein multiplied by the treatment time.

Based on the shortcomings of previously attempted methods for reducing or preventing redeposition, there is a need for more easily controlled and more cost effective methods to address the issue of redeposition or backstaining of dye during stonewash treatment.

Accordingly, it would be desirable to find an enzymatic composition or method that would be cost effective, have good shelf stability, high potency, and not include a redepositing or backstaining cellulase.

SUMMARY OF THE INVENTION

The inventors of the present invention ("the inventors") have found that washing cotton indigo-dyed denim with a low backstaining cellulase enzyme composition made by subjecting a Trichoderma cellulase that contains both cellobiohydrolase and endoglucanase enzymes to a limited proteolysis (i.e., a limited protease treatment) and subsequent removal of the added protease is an improvement over the use of a redepositing cellulase preparation or one that includes both a cellulase and a protease. The denim produced by treatment with such a composition unexpectedly has a reduced level of dye redeposition and hence good contrast between blue and white threads on the denim. The composition is shelf stable, requires significantly less protease than previous methods, and has a surprisingly low level of redeposition even though the "backstain inhibiting composition" (i.e., the protease) taught to be required by Clarkson et al is not present. The inventors have also provided methods to recover and recycle protease so that this expensive ingredient can be reused. In the denim washing process, a small percentage of surface active chemical surfactant may optionally be added to the compositions or methods described herein. If a surface active agent is added, it may be added either with the cellulase in the wash or as an after treatment rinse. In addition, the denim washing process may be carried out with or without stones added to the compositions described herein.

DETAILED DESCRIPTION OF THE INVENTION

Denim that is stonewashed with a Trichoderma cellulase enzyme composition that has been subjected to a limited protease treatment and subsequent purification to remove the protease shows a dramatic reduction in the level of backstaining and a visible increase in the contrast between white and blue threads. While the inventors do not wish to be held to any particular theory, one possible explanation for the apparently contradictory observations that, on the one hand protease is required in the washer (Clarkson et al) and that, on the other hand it need not be present (this invention), is that there are two separate and distinct mechanisms by which proteases may affect backstaining in a denim washing processes.

The first mechanism is that described by Clarkson et al, where the protease simply acts as a stain removing agent in the washer. This mechanism is consistent with Clarkson's findings that proteases can remove redeposited dye even after it has stained the white denim in a prior cellulase treatment. It is also consistent with the well known use of proteases as stain removers in detergent systems. Not surprisingly, the dye-based stains created by cellulase proteins can be removed by one of the well known approaches for treating stains related to proteins: proteases.

Under this first mechanism, however, those skilled in the art would not expect proteases to be able to mitigate against backstaining in the washer if they are never put in the washer. To explain the inventors' surprising finding that proteases seem to be able to do just that, the inventors suggest that there is a second mechanism that is more subtle and less obvious than the first. In particular, the inventors believe that a limited-protease treatment changes the mode of action of cellulase enzymes causing them to make small, easily dispersed particles that do not backstain. While it has been reported that proteases can render the cellobiohydrolase components present in the Trichoderma cellulase enzyme complex inactive against crystalline cellulose by cleaving off their natural cellulose binding domains, the inventors hypothesize that such a treatment may still leave the cellobiohydrolase enzymes capable of making small nicks in the cellulose which are not detectable on their own but, when used in combination with other components in the Trichoderma cellulase enzyme complex, i.e. the endoglucanases, lead to substantial abrasion in a denim washing environment. The inventors further suggest that, because the modified cellobiohydrolases do not have binding domains, their action against crystalline cellulose is likely to be less localized and more evenly distributed on the denim fibers than under treatment with the intact Trichoderma cellulase. For intact Trichoderma cellulase enzymes, their highly localized mode of action could lead to relatively large particles being released from the main body of the cellulose as the enzymes cut directly through large parts of the fiber. By contrast, the more distributed pattern of action of protease-treated Trichoderma cellulase compositions might lead to smaller, more easily dispersable particles being broken loose from the main body of the cellulose in an environment where there is a significant amount of shear or mixing. As a result, there would be less backstaining.

This second mechanism, although unrecognized, was probably playing a minor role in the combined cellulase and protease treatments described by Clarkson. It went unrecognized because prior workers focussed on exploiting the more obvious use of protease to remove stains in the washer. It was not fully exploited because, if one is planning to make a single commercial enzyme composition containing both cellulase and protease enzymes, it is difficult to operate the proteolysis reaction effectively. In Clarkson's own words, there is a difficult tradeoff and one must "balance between the proteolytic effect on reducing backstaining and the proteolytic effect on reducing abrasion". Thus, to make a combined cellulase/protease enzyme composition that can be added directly to a washer, those skilled in the art would certainly want to avoid the use of proteases like papain which are known to destroy activity on crystalline cellulose in favor of ones more known for their anti-staining properties in detergents, e.g. subtilisin.

Surprisingly, the inventors have found that better overall results are achieved by (1) abandoning the benefits of this first "anti-staining" mechanism (i.e. by removing the protease from the enzyme preparation and thereby the denim washing), and (2) taking advantage of this change to modify the conditions of the proteolytic reaction to get a stronger and more aggressive treatment and thereby maximize the impact of the previously unrecognized second mechanism. In all, the new compositions resulting from this approach permit superior and more cost effective washing of denim.

Prior to discussing this invention in further detail, the following terms will be defined.

The term "Trichoderma cellulase composition" comprises at least one or more of the cellobiohydrolase (CBH) enzymes, and one or more of the endoglucanase (EG) enzymes produced by the fungal microorganism *Trichoderma sp.* When the composition is produced by a naturally occurring Trichoderma microorganism, and each of these components is found at the ratio naturally produced by the microorganism, the composition is sometimes referred to herein as a "complete or natural Trichoderma cellulase composition."

It is contemplated that the Trichoderma cellulase compositions of the present invention may also refer to any cellulase composition containing both a cellobiohydrolase and endoglucanase that is obtained from a *Trichoderma sp.* that has been genetically modified so as to overproduce, underproduce or not produce one or more of the CBH, and/or EG components of cellulase. These endoglucanases and cellobiohydrolases may include not only enzymes that are a part of the natural Trichoderma cellulase enzyme composition, but also such modified cellulase compositions as truncated cellulase proteins comprising either the binding domain or the core domain of the CBHs or EGs, or a portion or derivative thereof. Other examples of modified cellulase compositions may include alterations in the degree of glycosylation, or substitution(s) of amino acid(s) in the primary structure of the cellulases or truncated cellulases. It is also contemplated that any natural or modified versions of natural Trichoderma cellulases, such as those outlined above, shall be considered Trichoderma cellulase compositions even if they are produced in a genetically modified host microorganism other than Trichoderma.

The term "protease-treated Trichoderma cellulase" refers to a Trichoderma cellulase composition in which a significant fraction of the CBH core domains have had their CBH binding domains cleaved off, for example with treatment by an added protease enzyme. The protease-treated Trichoderma cellulase compositions should not, however, have any significant incremental or residual active protease over the amount which is produced naturally by the microorganism. Such an incremental amount should, for example, be less than 0.1% of the total amount of protein in the cellulase enzyme composition.

It is contemplated that the protease-treated cellulase compositions of the present invention may include both preparations where an added protease enzyme is used to cleave the CBH core and binding domains as well as modified cellulase compositions where the CBH core domain is produced directly without its binding domain by a genetically modified microorganism. In all cases, though, a protease-treated Trichoderma cellulase composition should contain endoglucanase activity as well as CBH core protein.

The methods of the present invention comprise contacting denim to be partially or wholly enzymatically stonewashed with a protease treated Trichoderma cellulase composition in an amount sufficient to achieve the desired level of dye removal from the garment. The use of such an enzyme will result in a garment with excellent contrast between blue and white threads and a low level of backstaining. The enzyme itself will have good stability and be in no danger of significant protease degradation.

In one embodiment of this invention, the protease-treated Trichoderma cellulase composition is produced by contacting a Trichoderma cellulase composition with an added protease enzyme wherein the extent of treatment, as defined by the weight ratio of protease protein to cellulase protein multiplied by the average treatment time, is in the range between 1.0 g min/g and 10,000 g min/g. The protease is then removed from the cellulase using a chromatographic separation. In a further embodiment of this invention, this protease treated Trichoderma cellulase composition is added to a washing machine with indigo dyed denim and used to created an abraded appearance with a high contrast between the blue and white fibers of the denim.

Cellulase Enzymes

Trichoderma cellulase compositions are typically produced in submerged culture of the fungus Trichoderma and methods for their production and recovery are well documented in the literature and widely known to those skilled in the art.

Commercial sources for these enzymes include Iogen Corporation, Genencor International, Novo Nordisk, Gist-Brocades, Sigma Chemicals, and Enzyme Development Corporation.

One of the preferred Trichoderma cellulase compositions of this invention is that produced by strains of the fungus *Trichoderma longibrachiatum* in which the relative concentrations of the enzymes CBH1, CBH2, EG1, EG2, and EG3 are all essentially consistent with what is found in a complete or natural Trichoderma cellulase composition.

Commercial cellulase preparations are not 100% cellulase protein and often include fillers, buffers, stabilizers and other ingredients. Total cellulase protein can be measured by various assay methods known in the art. The assay preferably used herein is the commercially available Biorad Coomassie Blue Protein assay sold by the Biorad Company, Los Angeles, using highly purified cellulase protein as the standard.

Added Protease

Proteases are available from several sources including microbial, plant, and animal sources and are well documented in the literature. Some important microbial proteolytic sources include *Bacillus licheniformis*, *Bacillus subtilis*, and *Aspergillus oryzae*.

Important sources of plant proteases include papaya for papain, and pineapples for bromelain. Proteases suitable for the invention include serine, cysteine, aspartic acid and metallo proteases. One of the preferred proteases is the cysteine protease papain.

Proteases are readily available commercially from firms such as Sigma Chemicals in a number of different forms including as liquid solutions, powders, or as insoluble enzymes attached to solid supports. In a preferred embodiment of this invention, the protease papain is used in a liquid suspension.

Commercial protease preparations are not 100% protease protein and often include fillers, buffers, stabilizers and other ingredients. Total protease protein can be measured by various assay methods known in the art. The assay preferably used herein is the commercially available Biorad Coomassie Blue Protein assay sold by the Biorad Company, Los Angeles.

Protease Treatment

The limited protease treatment of this invention comprises contacting a liquid Trichoderma cellulase composition with an added protease under controlled reaction conditions for a defined period of time. One skilled in the art will recognize that the appropriate extent of treatment will depend upon the temperature, pH, concentration chosen to prepare the mixture and on the specific activity of the protease enzyme that has been selected and will further recognize that routine testing procedures can be used to select an optimum set of process conditions for a given cellulase composition and added protease.

In a preferred embodiment, the limited-protease treatment is carried out at an elevated temperature between 20° C. and 60° C. and more preferably between 30° C. and 50° C. In the most preferred embodiment, a temperature of about 37° C. is employed.

In a preferred embodiment, the limited protease treatment is carried out at a pH between 3.0 and 8.0 and more preferably between 4 and 7. In the most preferred embodiment, the pH is between 4 and 5.

In a preferred embodiment, the limited protease treatment is carried out with a concentration of cellulase protein between 5 and 250 g/l and more preferably between 50 and 200 g/l. In the most preferred embodiment, the cellulase protein concentration is about 100 g/l.

In a preferred embodiment, the limited protease treatment time is between 5 minutes and four weeks and more preferably between 1 and 120 hours. In the most preferred embodiment, where the protease is papain, the treatment time is about 24 to 48 hours.

In a preferred embodiment, the extent of treatment, as defined by the weight ratio of protease protein to cellulase protein multiplied by the average treatment time, is in the range between 1.0 g min/g and 10,000 g min/g and more preferably between 10 and 1,000 g min/g. In the most preferred embodiment, where the protease is papain, the extent of treatment is in the range of about 200 g min/g. Under these preferred conditions, this means that the concentration of the papain is about 14 gm/liter.

One preferred method of following the progress of a proteolysis reaction is to use the filter paper carboxymethylcellulose (CMC) assays which measure respectively filter paper units (FPUs) and carboxymethylcellulose units (CMCUs) of cellulase activity (Ghose, 1987). Preferrably the protease treatment would be run to an extent that the cellulase loses at least 5% of its initial activity as measured in filter paper units and not more than 50% of its initial activity as measured in CMC units. Even more preferrably, the cellulase should be treated to an extent that it loses at least 10% of its initial cellulase activity as measured in FPUs and maintains substantially between 70% and 100% of its initial activity as measured in CMCUs. Even more preferrably, the cellulase should be treated to an extent that it loses about 50% of its initial cellulase activity as measured in FPUs and less than 10% of its initial activity as measured in CMCUs.

Protease Removal and Recovery

The method of this invention further requires that the proteolytic reaction be stopped when it has reached the desired extent of treatment such that no significant amounts of exogenous protease contaminate the protease-treated Trichoderma cellulase enzyme composition of this invention. The reaction can be stopped, for example, by chilling or by adjusting the pH. The added protease can then be separated from the cellulase complex. One skilled in the art will recognize that there are a number of means to selectively remove added protease from a Trichoderma cellulase enzyme composition including chromatographic separation, selective precipitation, ultra-filtration, or filtration (if an insoluble enzyme on a solid support is used). The appropriate method of removal will depend upon the specific nature and form of the protease that has been selected for the treatment.

A preferred method of accomplishing this separation is to bind a dissolved protease to a solid material and then wash the cellulase away from it. One such binding medium used herein is a commercially available cation exchange resin, S-Sepharose, sold by Pharmacia Biotech, Uppsala, Sweden, which will bind many commercial protease enzymes when contacted with a solution of cellulase and protease at a pH below 6.0. A preferred method of using S-Sepharose, which is applicable for removing the protease papain from a Trichoderma cellulase enzyme preparation, is to dialyse a mixture of cellulase and protease to a conductivity of 3,000 μ-S or less and then pass it over an S-Sepharose resin at a pH of between 4.5 and 5.0 and a temperature below 20° C.

In a preferred embodiment, the protease is recovered and reused on another batch of Trichoderma cellulase. One preferred method of recovering the protease is to bind it to an S-Sepharose resin at a pH of between 4.5 and 5.0 and a temperature below 20° C. The S-Sepharose resin can bind approximately 100 gm/l of the protease papain. The cellulase/papain mixture is passed over the resin and when the resin is fully loaded with papain, it is washed with softened water to remove any contaminating cellulase and then washed with a 1M sodium chloride solution to desorb the papain. The papain solution is then dialysed to remove excess salt and is then ready for reuse. During this recovery operation it is important to maintain a reducing environment because papain is subject to a reversible oxidative inactivation.

Product Formulation

The cellulase compositions of this invention may also comprise various adjuvants as known to those skilled in the art. For example, a surfactant (anionic or nonionic) compatible with the cellulase composition would be useful in the compositions of the present invention. Preferable surfactants are nonionic, such as the polyoxyethylated alcohols found in the TRITON® series of surfactants (octylphenoxypolyethoxyethanol nonionic surfactants) which are commercially available from Union Carbide. It should be noted that inclusion of a surfactant may further improve the relative contrast between white and blue threads and reduce the amount of dye redeposition. Other materials can also be used with or placed in the composition as desired, including stones, fillers, solvents, buffers, enzyme stabilizers, pH control agents, enzyme activators, builders, other anti-redeposition agents and the like. The enzyme composition may be formulated as a solid product wherein the solid may be granular, spray dried or agglomerated. Alternatively, the enzyme composition may be formulated as a liquid, gel, or a paste product. A liquid preparation is preferred herein.

Denim Washing

The washing of denim to create a "stone washed" appearance can substantially be accomplished by using a stone or a stone free process in which the denim or denim garments are mechanically agitated in a washing machine with an aqueous composition containing the protease-treated Trichoderma cellulase compositions. The amount of the composition used to treat denim would depend on the concentration of cellulase protein in the cellulase composition, the amount of denim substrate in the washer, and the desired amount of stonewash effect, and other well-known parameters to those skilled in the art. The preferred amount of the protease-treated Trichoderma cellulase composition is generally between 500 and 200,000 CMC units of enzyme per kg of denim and more preferably between about 5,000 and 100,000 CMC units per kg of denim.

In a preferred embodiment, the denim washing treatment is carried out at an elevated temperature between 30° C. and 70° C. and more preferably between 45° C. and 55° C.

In a preferred embodiment, the denim washing treatment is carried out at a pH between 4.0 and 7.5 and more preferably between 4.5 and 6.5. In the most preferred embodiment, the pH for the denim treatment is about 6.0.

In addition to the cellulase composition, the denim washing step may also use a variety of other processing aids. For example, a surfactant (anionic or nonionic) compatible with the cellulase composition would be useful to be added to the washer in the methods of the present invention. Preferable surfactants are nonionic, such as the polyoxyethylated alcohols found in the TRITON® series of surfactants (octylphenoxypolyethoxyethanol nonionic surfactants) which are commercially available from Union Carbide. It should be noted that inclusion of a surfactant further improve the relative contrast between white and blue threads and reduce amount of dye redeposition. Other materials can also be used with or placed in the washer as desired, including stones, fillers, solvents, buffers, enzyme stabilizers, pH control agents, enzyme activators, builders, other anti-redeposition agents and the like.

EXAMPLES

The above specification provides a discussion of the compositions of the invention and methods of making and using the compositions in the "stone-washing" of fabric clothing items. The following Examples provide specific details with respect to the compositions and methods of the invention. Other choices of added protease and cellulase, as well as wash conditions such as concentration, measurement, pH, temperature, and the like, will be evident to those skilled in the art based on the teachings herein.

Example 1

Preparation of a Protease Treated Trichoderma Cellulase Composition

Approximately 600 liters of a natural Trichoderma cellulase preparation was produced by the fermentation of *Trichoderma longibrachiatum* and dialysed to a conductivity of 450 μ-S. While this product was not stabilized or preserved, it is available in a stabilized and preserved form as Iogen Cellulase from Iogen Corporation. A substantially similar material can be prepared by simply dialysing Iogen Cellulase to remove stabilizers and preservatives. It was then concentrated to a volume of 500 liters by ultra filtration. The resulting dialysed product has a protein concentration of 140 gm/l and an endoglucanase activity of 1599 CMC units/ml using the method of Ghose (1987). 150 liters of the preparation was removed and the remaining preparation was then mixed with 150 liters of soft water and 40 kg of Biocon papain powder available from Quest International (Product number 5x98490) and having a protein concentration of 105 g/kg and an activity of 1,000 milk clotting units (MCU)/mg of papain powder as specified by Quest International. The pH was adjusted to 4.8 using sodium benzoate and the mixture was incubated at roughly 35° C. to 40° C. for 42 hours. The resulting extent of treatment was approximately 216 g min/g. 49% of the initial cellulase activity was lost during this protease treatment as measured in FPUs and less than 10% as measured in CMCUs. The mixture was then chilled to roughly 20° C. over a period of one hour. The mixture was then clarified on a diatamaceous earth precoated plate and frame filter. With rinse water, the preparation was diluted to a volume of roughly 960 liters. Protease was removed from the protease and cellulase mixture by passing the preparation over an S-Sepharose cation exchange resin according to the instructions of the resin manufacturer (Pharmacia Technical Manual 18-1022-19 "Ion Exchange Chromatography: Principles and Methods", 1991). S-Sepharose was first equilibrated to pH 4.7 with acetate buffer; subsequently, the protease/cellulase mixture was loaded to the resin to the extent of approximately 13 g papain protein per liter of packed resin. The resin was washed with pH 4.7 acetate buffer. The combined effluents from the column loading and washing phases consisted of pure papain-free cellulase: the activity of papain in the cellulase was below detection limits based on activity against azo-casein. The S-Sepharose bound papain was subsequently recovered by passing 1.0M sodium chloride, pH 4.8, over the resin. The volume of the protease-treated Trichoderma cellulase preparation was about 2,700 liters. The resulting protease-treated Trichoderma cellulase preparation was preserved by adjusting its pH to 4.0 and adding sodium benzoate to 0.5%. This composition was then concentrated by ultrafiltration and stabilized conventionally ("Enzyme Applications", Encyclopedia of Chemical Technology, Vol. 9, Fourth Edition, 1994) to a final concentration of approximately 1,800 CMC units/ml.

Example 2

Denim Washing with a Protease Treated Trichoderma Cellulase Compostion

A 35 lb. UniMac Washer/Extractor machine was used. Approximately 5.1 kg of desized denim garment was placed in the machine. The denim consisted of 3 sewn pant legs, of 30 cm. length and 5 one meter square pieces of Swift 14 oz. #37628 denim, and 3 sewn pant legs of 30 cm. length of Swift 12 oz. #25113 denim, all made by Swift, Drummondville, Quebec. The denim was desized by treating for 15 minutes at 70° C. with 30 g of Rapidase UC alpha-amylase enzyme, available from Gist-Brocades. The machine was filled with 51 liters of hot water and brought to 50° C. The liquor ratio was 10:1 (weight of liquor to weight of garments). The liquor was buffered to pH 6.0 with 300 grams of 85% phosphoric acid and 114 grams of sodium hydroxide pellets.

The machine was agitated for 1 minute to disperse the buffer and establish the temperature. At this point, 70 ml of the protease-treated cellulase preparation of Example 1 was added to the machine. The garments were washed at 47 RPM for 60 minutes. After this, the bath was dropped.

The bath was then filled with 50° C. water and 2 g/L of soda ash was added to adjust the pH up to 9.0 to 11.0 to destroy the cellulase activity. The machine was agitated for 10 minutes and then the bath was dropped. The garments were then rinsed with cold water for 5 minutes and hot water for 30 seconds. This was followed by two 10-minute rinses at 50° C., then the bath was dropped and spun down. The garments were then dried in a standard household dryer for 30 minutes. The garments were then removed from the dryer and ironed without steam.

Brightness readings were taken off the denim using an Elrephro brightness meter. The brightness readings of the #37628 pant leg were used to estimate net dye removal and were converted to net amount of indigo dye removal from the fabric by comparing with samples of known indigo content. Results are reported as a percent of the indigo in unwashed denim. The brightness readings of the #25113 pant leg were used to estimate degree of backstaining and were converted to net amount of indigo dye redeposited onto the fabric by comparing with samples of known indigo content. Results are reported as a percent of the indigo in unwashed denim.

The procedure was repeated with 88 ml of Iogen Cellulase, a standard redepositing cellulase enzyme. The results were as shown in Table 1.

TABLE 1

Comparison of protease treated and non treated Trichoderma cellulase.

| | Net Dye Release | Backstaining |
|---|---|---|
| Protease treated Cellulase | 19.2% | 2.8% |
| Iogen Cellulase | 21.4% | 8.3% |

As is apparent from Table 1 for roughly the same degree of dye removal, denim exposed to the protease-treated cellulase exhibits much less backstaining than the redepositing cellulase.

Example 3

Denim Washing with Added Surfactant

Using the procedures described in Example 2 except as noted, the following enzymes were used in washing the denim:

a. 80 ml of protease-treated Trichoderma cellulase from Example 1, used as in Example 2.
b. 80 ml of protease-treated Trichoderma cellulase from Example 1, used as in Example 2 except that 40 ppm of TRITON® X100 was added to the washer at the start of the cellulase washing.
c. 80 ml of protease-treated Trichoderma cellulase from Example 1, used as in Example 2 except that 80 ppm of TRITON® X100 was added to the washer at the start of the cellulase washing.
d. 80 ml of protease-treated Trichoderma cellulase from Example 1, used as in Example 2 except that 160 ppm of TRITON® X100 was added to the washer at the start of the cellulase washing.

TABLE 2

Demonstration of the effect of added surfactant.

| | Net Dye Release | Backstaining |
|---|---|---|
| Protease treated Cellulase (0 ppm TRITON ® X100) | 21.46% | 2.81% |
| Protease treated Cellulase (40 ppm TRITON ® X100) | 21.09% | 2.29% |
| Protease treated Cellulase | 20.08% | 2.22% |

TABLE 2-continued

Demonstration of the effect of added surfactant.

| | Net Dye Release | Backstaining |
|---|---|---|
| (80 ppm TRITON ® X100) | | |
| Protease treated Cellulase (160 ppm TRITON ® X100) | 17.72% | 2.09% |

As Table 2 demonstrates, the addition of surfactant further reduces backstaining without significant loss of net dye release.

Example 4

Comparative Denim Washing Results

Using the procedures described in Example 2, the following enzymes were used the washing denim:

a. Protease-treated cellulase from Example 1 and tested in Example 2.
b. Following the protocols of Clarkson et al, Iogen Cellulase (which consists of 142 mg/ml of protein) was added as the redepositing Trichoderma cellulase and respectively 0.02 ml, 0.10 ml, 0.5 ml, 2.5 ml, and 12.5 ml of Rapidase WSL-2 subtilisin, available from Gist-Brocades; was added as the protease. This protease consists of 110 mg/ml of protein. The amount of Iogen Cellulase used was 88ml, except for the run with 12.5 ml protease, which had 78 ml cellulase. The levels of protease addition were respectively 0.02%, 0.08%, 0.40%, 2.0% and 10% of weight of subtilisin protein to weight of cellulase protein. The minimum desirable level taught by Clarkson et al was 0.1%. As suggested by Clarkson et al, the pH in the washer was adjusted to 5.0 with 152 g glacial acetic acid and 55 g sodium hydroxide pellets. All of the other procedures were as in Example 2.

The results are listed in Table 3 and show that the protease-treated Trichoderma cellulase composition gave denim a much lower level of backstaining than the method of Clarkson et al. While the results contradict the Clarkson et al teaching of the need for protease in the wash, they do support their teachings that when cellulase and protease are added together to the washing machine, the backstaining is significantly decreased with more than 0.1% protease relative to cellulase present.

TABLE 3

Comparison of non-redepositing cellulase enzyme compostions.

| | Net Dye Release | Backstaining |
|---|---|---|
| Protease treated Cellulase | 19.2% | 2.8% |
| Clarkson et al (0.02%) | 23.8% | 13.6% |
| Clarkson et al (0.08%) | 24.7% | 9.7% |
| Clarkson et al (0.4%) | 28.4% | 6.1% |
| Clarkson et al (2.0%) | 24.8% | 6.2% |
| Clarkson et al (10.0%) | 23.6% | 7.1% |

Example 5

Further Preparation of Protease Treated Trichoderma Cellulase Compositions

Approximately 1,000 liters of a natural Trichoderma cellulase preparation was produced by the fermentation of

*Trichoderma longibrachiatum* and dialysed to a conductivity of 310 μS. While this product was not stabilized or preserved, it is available in a stabilized and preserved form as Iogen Cellulase from Iogen Corporation. A substantially similar material can be prepared by simply dialysing Iogen Cellulase to remove stabilizers and preservatives. It was then concentrated to a volume of 725 liters by ultrafiltration. The resulting dialysed product had a protein concentration of 98 gm/l and an endoglucanase activity of 1325 CMC units/ml using the method of Ghose (1987). 375 liters of the preparation was removed and the remaining preparation was then mixed with 150 liters of soft water and 15.75 kg of "Folexco Papain 300MCU" available from Folexco Incorporated and having a concentration of active papain protein estimated at 32 g/kg and an estimated activity of 300 milk clotting units (MCU)/mg of papain powder. The pH was adjusted to 4.8 using sodium benzoate and the mixture was incubated at roughly 35° C. to 50° C. for 27 hours. The resulting extent of treatment was approximately 24 g min/g. The inventors estimate that roughly 20% of the FPU activity and none of the CMCU activity was lost during this protease treatment. The mixture was then chilled to roughly 10° C. over a period of two hours. The mixture was then clarified on a diatamaceous earth precoated plate and frame filter. With rinse water, the preparation was diluted to a volume of roughly 800 liters. Protease was removed from the protease and cellulase mixture by passing the preparation over an S-Sepharose cation exchange resin according to the instructions of the resin manufacturer (Pharmacia Technical Manual 18-1022-19 "Ion Exchange Chromatography: Principles and Methods", 1991). S-Sepharose was first equilibrated to pH 4.7 with acetate buffer; subsequently, the protease/cellulase mixture was loaded to the resin to the extent of approximately 5 g papain protein per liter of packed resin. The resin was washed with pH 4.7 acetate buffer. The combined effluents from the column loading and washing phases consisted of pure, papain-free cellulase: the activity of papain in the cellulase was below detection limits based on activity against azo-casein. The S-Sepharose bound papain was subsequently recovered by passing 1.0M soduim chloride, pH 4.8, over the resin. The volume of the protease treated Trichoderma cellulase preparation was about 1,600 liters. The resulting protease treated Trichoderma cellulase preparation was preserved by adjusting its pH to 4.0 and adding sodium benzoate to 0.5%. This composition was then concentrated by ultrafiltration and stabilized conventionally ("Enzyme Applications", Encyclopedia of Chemical Technology, Vol. 9, Fourth Edition, 1994) to a final concentration of approximately 2,000 CMC units/ml.

Example 6

Denim Washing with Protease-treated Trichoderma Cellulase Compositions

Using the procedures described in Example 2 except as noted, the following enzymes were used in washing denim:

a. 86 ml of protease-treated Trichoderma cellulase from Example 5, used as in Example 2.

b. 70 ml of protease-treated Trichoderma cellulase from Example 1 as tested in Example 2.

c. 88 ml of Iogen Cellulase as described and tested in Example 2.

The results are listed in Table 4 and demonstrate that the lower levels of papain treatment employed in Example 5 (24 g min/g) do not give quite so good performance as the more harsh treatments of Example 1 (216 g min/g).

TABLE 4

Comparison of protease treated and non treated Trichoderma cellulase.

|  | Net Dye Release | Backstaining |
|---|---|---|
| Protease treated Cellulase (Example 5) | 18.0% | 3.8% |
| Protease treated Cellulase (Example 1) | 19.2% | 2.8% |
| Iogen Cellulase | 21.4% | 8.3% |

Example 7

Comparative Denim Washing Results

Using the procedures described in Example 2, the following enzymes were used in washing denim:

a. Protease-treated cellulase from Example 1 and tested in Example 2.

b. 80 ml of protease-treated Trichoderma cellulase from Example 1, as tested in Example 3 with 40 ppm of TRITON® X100 added to the washer at the start of the cellulase washing.

c. Euro L, a commercial cellulase product of Genencor International that we believe contains protease enzyme, a redepositing Trichoderma cellulase and a surfactant, was added at an amount of 100 ml. As per the manufacturers suggestion, the pH was adjusted to 5.5 with 150 g of glacial acetic acid and 85 g of sodium hydroxide pellets. All other procedures were as in Example 2.

d. Euro L was added to the washer at an amount of 100 ml. 40 ppm of TRITON® X100 was also added to the washer at the start of the cellulase washing. As per the manufacturers suggestion, the pH was adjusted to 5.5 with 150 g of glacial acetic acid and 85 g of sodium hydroxide pellets. All other procedures were as in Example 2.

e. Denimax L, a commercial product of Novo Nordisk that we believe contains low-backstaining enzyme mage by *Humicola insolens* was added at an amount of 250 ml. As per the manufacturer's suggestion, the pH was adjusted to 6.5 with 297 g of phosphoric acid and 125 g of sodium hydroxide pellets. All other procedures were as in Example 2.

f. Denimax L was added to the washer at an amount of 250 ml. 40 ppm of TRITON® X100 was also added to the washer at the start of the cellulase washing. As per the manufacturer's suggestion, the pH was adjusted to 6.5 with 297 g of phosphoric acid and 125 g of sodium hydroxide pellets. All other procedures were as in Example 2.

The results are listed in Table 3 and show that, for similar dye release, the protease-treated Trichoderma cellulase composition gives denim a lower level of backstaining than the Euro L or the Denimax L. This good performance of the protease treated Trichoderma cellulase without surfactant relative to Euro L is achieved even though Euro L contains performance enhancing surfactants. The low potency of the *Humicola insolens* cellulase is evident from the fact that 2 to 3-fold more Denimax L was required to fade the denim than with the other enzymes.

TABLE 3

Comparison of non-redepositing cellulase enzyme compositions.

| | Net Dye Release | Backstaining |
|---|---|---|
| Protease treated Cellulase | 19.2% | 2.8% |
| Protease treated Cellulase (40 ppm TRITON ® X100) | 21.09% | 2.29% |
| Euro L | 19.9% | 3.4% |
| Euro L (40 ppm TRITON ® X100) | 21.44% | 3.35% |
| Denimax L | 19.6% | 3.6% |
| Denimax L (40 ppm TRITON ® X100) | 18.17% | 3.32% |

While preferred embodiments of our invention have been shown and described, the invention is to be defined solely by the scope of the appended claims.

We claim:

1. A cellulase enzyme composition that produces low backstaining of indigo-dyed denim relative to a natural Trichoderma cellulase, the enzyme composition comprising a protease-treated Trichoderma cellulase that is a product of a process comprising:
   a. subjecting a Trichoderma cellulase containing a cellobiohydrolase enzyme and an endoglucanase enzyme to a limited protease treatment by adding a protease to the cellulase, the limited protease treatment being defined by using a weight ratio of protease to cellulase multiplied by an average treatment time that is substantially between 1.0 and 10,000 gram minutes per gram,
   b. stopping the protease reaction by chilling or adjusting the pH, and
   c. purifying the cellulase by substantially removing the added protease so as to define the composition.

2. The composition composition according to claim 1, wherein said protease treats the cellulase to an extent that the treated cellulase loses at least 5% of its initial activity as measured in filter paper units (FPUs) and no more than 50% of initial activity as measured in carboxymethylcellulose CMC units.

3. The composition according to claim 1 wherein the protease treats the cellulase to an extent that the treated cellulase maintains substantially between 15% and 90% of its initial activity as measured in FPUs, and maintains substantially between 70% and 100% of its initial activity as measured in CMC units.

4. The composition according to claim 1 wherein the extent of said limited protease treatment step is defined by using a weight ratio of protease to cellulase multiplied by an average treatment time that is substantially between 10.0 and 5,000 g min/g.

5. The composition according to claim 1 wherein the added protease comprises a papain protease.

6. The composition according to claim 1 wherein the added protease remaining the composition after the purification step is less than 0.1%, by weight of the composition, as measured by total protein content.

7. The composition according to claim 1 wherein the added protease remaining in the composition after the purification step is less than 0.05%, by weight of the composition, as measured by total protein.

8. The composition according to claim 1 wherein no detectable added protease remains in the composition after the purification step.

9. A composition according to claim 1, wherein the Trichoderma cellulase to be treated further comprises endoglucanase (EG) enzyme and cellobiohydrolase (CBH) core domains, wherein at least some of the CBH core domains are not linked to their natural binding domains and wherein the composition defined has substantially no incremental or residual protease activity over the amount which is produced naturally by the Trichoderma.

10. A composition according to claim 9, wherein said cellulase to be treated further is made by a strain of Trichoderma that was genetically modified to produce directly at least some of the CBH core domains which are not linked to their natural binding domains.

11. A cellulase enzyme composition that produces low backstaining of indigo-dyed denim relative to a natural Trichoderma cellulase, the enzyme composition comprising a protease-treated Trichoderma cellulase that is a product of a process comprising:
   (a) subjecting a Trichoderma cellulase containing a cellobiohydrolase enzyme and an endoglucanase enzyme to a limited protease treatment by adding a protease to the cellulase, the limited protease treatment being defined by using a weight ratio of protease to cellulase multiplied by an average treatment time that is substantially between 1.0 and 10,000 gram minutes per gram, and immediately,
   (b) purifying the cellulase by substantially removing the added protease so as to define the composition.

12. The composition according to claim 11, wherein said protease treats the cellulase to an extent that the treated cellulase loses at least 5% of its initial activity as measured in filter paper units and no more than 50% of its initial activity as measured in CMC units.

13. The composition according to claim 11 wherein the protease treats the cellulase to an extent that the treated cellulase maintains substantially between 15% and 90% of its initial activity as measured in FPUs, and maintains substantially between 70% and 100% of its initial activity as measured in CMC units.

14. The composition according to claim 11 wherein the extent of said limited protease treatment step is defined by using a weight ratio of protease to cellulase multiplied by an average treatment time that is substantially between 10.0 and 5,000 g min/g.

15. The composition according to claim 11 wherein the added protease comprises a papain protease.

16. The composition according to claim 11 wherein the added protease remaining in the composition after the purification step is less than 0.1% by weight of the composition, as measured by total protein content.

17. The composition according to claim 11 wherein the added protease remaining in the composition after the purification step is less than 0.05%, by weight of the composition, as measured by total protein.

18. The composition according to claim 11 wherein no detectable added protease remains in the composition after the purification step.

19. A cellulase enzyme composition that produces low backstaining of indigo-dyed denim relative to a natural Trichoderma cellulase, the enzyme composition comprising a protease-treated Trichoderma cellulase that is a product of a process comprising:
   (a) subjecting a Trichoderma cellulase containing a cellobiohydrolase enzyme and an endoglucanase enzyme to a limited protease treatment by adding a protease to the cellulase, the limited protease treatment being defined by using a weight ratio of protease to cellulase multiplied by an average treatment time that is substantially between 1.0 and 10,000 gram minutes per gram, and (b) stopping the protease reaction by chilling or adjusting the pH.

20. The composition according to claim 19, wherein said protease treats the cellulase to an extent that the treated cellulase loses at least 5% of its initial activity as measured in filter paper units and no more than 50% of its initial activity as measured in CMC units.

21. The composition according to claim 19, wherein the protease treats the cellulase to an extent that the treated cellulase maintains substantially between 15% and 90% of its initial activity as measured in FPUs, and maintains substantially between 70% and 100% of its initial activity as measured in CMC units.

22. The composition according to claim 19, wherein the extent of said limited protease treatment step is defined by using a weight ratio of protease to cellulase multiplied by an average treatment time that is substantially between 10.0 and 5,000 g min/g.

23. The composition according to claim 19, wherein the added protease comprises a papain protease.

* * * * *